US012403246B2

United States Patent
Streit et al.

(10) Patent No.: US 12,403,246 B2
(45) Date of Patent: Sep. 2, 2025

(54) PIERCING DEVICE FOR AN ADMINISTRATION DEVICE

(71) Applicant: TecMed AG, Burgdorf (CH)

(72) Inventors: Ursina Streit, Schönbühl (CH); Patrick Hostettler, Hasle (CH); Christophe Hofer, Burgdorf (CH); Roland Margot, Worb (CH)

(73) Assignee: TecMed AG, Burgdorf (CH)

( * ) Notice: Subject to any disclaimer, the term of this patent is extended or adjusted under 35 U.S.C. 154(b) by 1155 days.

(21) Appl. No.: 17/227,081

(22) Filed: Apr. 9, 2021

(65) Prior Publication Data

US 2021/0228799 A1 Jul. 29, 2021

Related U.S. Application Data

(63) Continuation of application No. PCT/IB2019/058017, filed on Sep. 23, 2019.

(30) Foreign Application Priority Data

Oct. 10, 2018 (EP) .................................... 18199475

(51) Int. Cl.
*A61M 5/142* (2006.01)
(52) U.S. Cl.
CPC ............... *A61M 5/14248* (2013.01); *A61M 2005/14252* (2013.01); *A61M 2005/14268* (2013.01); *A61M 2205/3673* (2013.01)
(58) Field of Classification Search
CPC ...... A61M 5/14248; A61M 2205/3673; A61M 2005/14252; A61M 2005/1585;
(Continued)

(56) References Cited

U.S. PATENT DOCUMENTS 6,045,534 A 4/2000 Jacobsen et al.
9,220,838 B2 12/2015 Soma et al.
(Continued)

FOREIGN PATENT DOCUMENTS

EP 1549382 B1 3/2016
EP 3636298 A1 4/2020
WO 2020074988 A1 4/2020

OTHER PUBLICATIONS

International Search Report and Written Opinion received for International Patent Application No. PCT/IB2019/058017, mailed on Dec. 4, 2019, 9 pages.
(Continued)

*Primary Examiner* — Michael J Tsai
*Assistant Examiner* — Kathleen Paige Farrell
(74) *Attorney, Agent, or Firm* — Dorsey & Whitney LLP (57) ABSTRACT

A piercing device for an administration device includes an elastic element with which a biasing force may be generated for piercing, a base, and a cannula unit which may be movable relative to the base in a piercing direction from a safety (secured) position, where the cannula unit may be subjected to the biasing force in the piercing direction. The administration device further includes a securing element by which the cannula unit, subjected to the biasing force, may be held in the safety position and which has a thermosensitive region that may be deformable under mechanical stress when heated, and a heating element with which the thermosensitive region of the securing element may be heated, such that the thermosensitive region of the securing element may deform in response to the biasing force and, as a result, the cannula unit may move away from the safety position in the piercing direction.

15 Claims, 7 Drawing Sheets

(58) Field of Classification Search
CPC .......... A61M 2005/14268; A61M 2205/3653;
A61M 5/158; A61M 2005/206; A61M
2005/1581; A61M 5/14244; A61M 5/3287
See application file for complete search history.

(56) References Cited

U.S. PATENT DOCUMENTS

| | | | |
|---|---|---|---|
| 2009/0099521 A1* | 4/2009 | Graveson et al. | ............................ A61M 5/14248 |
| 2010/0152674 A1 | 6/2010 | Kavazov et al. | |
| 2012/0209183 A1* | 8/2012 | Gray | .................... G05D 7/0676 604/131 |
| 2014/0207104 A1* | 7/2014 | Vouillamoz | ........... A61M 5/158 604/179 |
| 2016/0367751 A1* | 12/2016 | Bazargan | ................ F04B 51/00 |
| 2019/0015580 A1* | 1/2019 | Oakes et al. | ....... A61M 5/14244 |
| 2019/0134309 A1* | 5/2019 | Wendland et al. | ........................... A61M 5/14248 |
| 2019/0366011 A1* | 12/2019 | Ring | ................. A61M 5/14248 |
| 2020/0316314 A1* | 10/2020 | Buri | .................... A61M 5/3287 |
| 2023/0226271 A1* | 7/2023 | Lanigan et al. | .. A61M 5/14248 |

OTHER PUBLICATIONS

International Preliminary Report on Patentability received for International Application No. PCT/IB2019/058017, mailed on Apr. 8, 2021, 8 pages.

* cited by examiner

PIERCING DEVICE FOR AN ADMINISTRATION DEVICE

CROSS-REFERENCE TO RELATED APPLICATIONS

This application claims priority to International Patent Application No. PCT/IB2019/058017, filed Sep. 23, 2019, entitled "PIERCING DEVICE FOR AN ADMINISTRATION DEVICE," which in turn claims priority to European Patent Application No. 18199475.7, filed Oct. 10, 2018, entitled "PIERCING DEVICE FOR AN ADMINISTRATION DEVICE", each of which is incorporated by reference herein, in the entirety and for all purposes.

TECHNICAL FIELD

Disclosed are medical administration devices for administering liquid substances, in particular medicaments or medicinal substances such as insulin and hormone preparations, by means of a cannula which is introduced into a body, and piercing devices with which a cannula may be automatically pierced into a body, for example by extending it from an administration device or from a cannula housing. After the cannula has penetrated a body, a medicinal substance may be dispensed into the body in a metered manner through the cannula.

BACKGROUND

A syringe, an injection pen or an infusion pump is often used to administer a medicinal substance or liquid. The infusion pump may be connected to an infusion set in order to dispense the substance or liquid into the patient's body tissue in a dosed manner. One possibility for the controlled administration of the substance is the delivery by a portable pump which the user carries on him or which is attached directly onto his skin. The latter is also known as a patch pump. In both cases, the substance to be dispensed is dispensed by the pump through a cannula inserted into the body of the user. The cannula may be introduced manually, for example by means of a known infusion set. As an alternative to the manual insertion of a cannula, automatic piercing devices are also known.

EP 1 549 382 B1 discloses, for example, a piercing device for a patch pump. The piercing device includes a flexible and a rigid cannula, the rigid cannula being located in the interior of the flexible cannula. The piercing device further includes a displaceable driver element which is connected to the flexible cannula and a displaceable retraction element which is connected to the rigid cannula. When a "shape memory" element is moved by means of electrical actuation, a locking element is shifted, which allows a biased (or prestressed) piercing spring to relax and thereby moves the driver element together with the retraction element out of the housing, whereby the two cannulas are pierced into the patient's skin. The driver element includes flexible fingers which protrude radially from the cannulas and which couple the retaining element to the driver element during the piercing process. However, as soon as the driver element is fully extended, a form fit is released and the flexible fingers may detach from the retaining element. As a result, a compressed retraction spring arranged coaxially to the piercing spring may relax and thus move the retraction element together with the rigid cannula back into the housing towards the holding element. Thus, the rigid cannula is withdrawn from the skin while the flexible cannula remains in the skin and allows a fluid path from a reservoir of the pump into the skin.

"Shape memory" elements, mechanical actuators or else thermal elements are used, as described, for example, in U.S. Pat. No. 9,220,838 B2. This discloses a piercing device in which a cannula is biased in a housing by a piercing spring, the piercing spring being prevented from relaxing and advancing the cannula by a retaining part. The retaining part is a rotatable lever, which in turn is acted upon with a force by a further release spring in the release direction. The rotatable retaining part is held in the blocking position by an actuator against the force of the release spring, and after actuation of the actuator and release of the retaining part, the retaining part is pulled by the release spring from the blocking position into a release position, so that the piercing spring may relax and the cannula may be inserted. In one embodiment, the actuator for retaining the retaining part against the force of the release spring may be a hook element which is connected to a melting part around which a wire in the form of a heating coil is wrapped. If an electric current flows through the wire, the melting part melts, so that the retaining part is rotated around an axis of rotation due to the force of the release spring and the piercing spring is functionally released.

Such known trigger mechanisms of piercing devices have the disadvantage that they require an expensive mechanical actuator or—in the case of a thermal actuator—require a complex construction which requires a lot of space.

SUMMARY

It is an object of the present disclosure to enable a cannula unit to be triggered in a piercing (or puncturing) device in a simple and cost-effective manner. This object is achieved by a piercing device and an administration device disclosed herein. According to the implementations of the present disclosure, the piercing device includes an elastic element with which a bias (or prestressing) force for piercing may be generated, a base on which the elastic element may be supported at one end, a cannula unit movable relative to the base from a secured (or safety) position in a piercing direction, whereby the cannula unit may be subjected to the biasing force in the piercing direction. The piercing device further includes a securing element, which may hold the cannula unit acted upon by the biasing force in the secured position and has a thermosensitive area which may be deformable when heated under mechanical stress, and a heating element with which the thermosensitive area of the securing element may be heated so that the thermosensitive area of the securing element may deform due to the biasing force. As a result, the cannula unit may move away from the secured position in the piercing direction.

According to the implementations of the present disclosure, the biasing force of an elastic element, which acts on the cannula unit with the biasing force in the piercing direction, may be at least partially transmitted to a securing element. This at least partial transmission of the biasing force may be carried out indirectly via at least one further element such as a transmission element or retaining element. However, the biasing force may just as well be transmitted directly from the cannula unit to the securing element. In any case, the securing element may be configured to hold the cannula unit acted upon or preloaded by the biasing force in a secured position against the biasing force. The cannula unit may be held by the securing element by means of a force fit, form fit or a combination of force fit and form fit. There may be a form-fitting connection between the securing element and the cannula unit. For this purpose, the securing element may have, for example, a tab, a hook, a pin or a receptacle for a correspondingly shaped counter element. If a further element such as a transmission element or retaining element may be arranged between the securing element and the cannula unit, the above-mentioned connections may be implemented both between the securing element and the further element and between the further element and the cannula unit. As a result of the at least partial transfer of the biasing force from the elastic element to the securing element, the latter may be under mechanical stress in the form of tensile, compressive, bending or torsional stress or a combination of these types of stress (multi-axis stress states). The securing element may be fastened with one end to the base, a support or holder and interacts with the other end directly or indirectly via a further element with the cannula unit.

In order to trigger the piercing process so that the cannula may be pierced into the skin of the user, the thermosensitive area of the securing element may be heated by means of the heating element. As a result of the heating, the thermosensitive area may deform by stretching or the thermosensitive area may tear apart completely. As a result, the cannula unit may no longer be held in the secured position by the securing element. This means that the locking or holding function of the securing element may be canceled. The biased elastic element may subsequently relax at least partially and move the cannula unit out of the secured position in the piercing direction. The elastic element moves the cannula unit either directly or indirectly via an intermediate element in the piercing direction. The cannula unit may move together with a cannula into a piercing position in which the cannula pierces the user's skin with its piercing end. A fluid which enters the cannula, for example, at an end of the cannula facing away from the piercing site, may flow through the cannula and exits at the cannula exit opening under the skin of the user.

Thus, triggering the piercing process only requires an actuator in the form of a heating element. This means that the energy stored by the biasing of the elastic element may not only be used to insert the cannulas but also for the release process. As a result, an actuator such as a servomotor, a solenoid coil or a separate mechanical spring, which moves the securing element, may not be required to release the cannula unit from the secured position. With the piercing device according to the implementations of the present disclosure, a part of the biasing force or biasing energy provided for piercing may be used directly in order to move the securing element and thus trigger the piercing process. In addition, triggering with the heating element may be implemented with fewer components than, for example, triggering with a solenoid coil or some other electromechanical actuator. In addition, the triggering with the heating element with the biasing force enables a compact configuration, since the heating element may be made very small, namely in the range of a few millimeters. This may enable a simple, inexpensive and also compact construction of the release mechanism and thus of the piercing device.

An element of the cannula unit may include a surface oriented obliquely to the piercing direction and the securing element or a transmission element interacting with the securing element may include a securing surface oriented obliquely to the piercing direction. If the securing element may be deformed or torn, for instance under tension, by heating and thereby freeing the cannula unit, the inclined surface of the cannula unit may be pressed onto the securing surface, as a result of which the surfaces that are inclined to the piercing direction and thus to the direction of movement of the cannula unit slide off one another or slide on one another, so that the cannula unit driven by the elastic element may move the securing element or the transmission element to the side.

In the present disclosure, the term "administration device" may be understood to mean a device in which the injection needle remains in the patient permanently or for a longer period of several hours. Such an administration device may be also referred to as an infusion system. Thus, in the case of an infusion system, in contrast to an injection system or injector, the injection needle may not be immediately removed from the user's tissue after the medical substance has been dispensed. An exception to this definition may be provided by so-called patch injectors, which in connection with the implementations of the present disclosure also fall under the term "administration device". A patch injector may be stuck to the user's skin, with a cannula or injection needle being pierced into the user's skin. The patch injector may remain on the skin, usually several minutes, until the medicinal substance has been delivered to the user from the patch injector.

The administration device according to implementations of the present disclosure may be an infusion system. Furthermore, the piercing process with the piercing device according to implementations of the present disclosure may be triggered electronically by means of a control command.

The elastic element for generating the biasing or prestressing force may for example be configured as a mechanical tension, compression or torsion spring but also in the form of a compressible liquid or an elastic plastic such as an elastomer.

The cannula unit may include at least one cannula which may be introduced under the skin of the user. Furthermore, the cannula unit may include a cannula holder on which the cannula may be fastened and which may be moved relative to a cannula housing or the base of the administration device together with an area of the cannula on the one side. By moving the cannula holder together with the cannula, a single-sided area of the cannula may be pierced into the user's skin.

In some embodiments, the cannula unit includes a hard and a soft cannula, which may be arranged coaxially to one another. The cannula unit may also include a hard and a soft cannula holder. In some embodiments, the hard cannula may be pierced into the skin together with the soft cannula and then the hard cannula may be pulled out of the piercing site again, while the soft cannula remains in the skin. In this case, at least during the piercing process, either the soft cannula surrounds the hard cannula or the hard cannula surrounds the soft cannula. The outer cannula (hard or soft cannula) may lie with its inner circumference in a sealing manner on the outer circumference of the hard cannula, so that no fluid may pass through. The inner cannula (hard or soft cannula) may be displaceable within the outer cannula. In some embodiments, soft and hard cannulas may be bendable, thus for example may be bent or curved in their longitudinal direction, so that a direction of movement of the cannula unit may be different from a direction of movement of the cannula tip. If a course of the hard and soft cannula assumes a curved or arched course, the hard cannula may be plastically deformed during the piercing process. In an alternative embodiment, however, the hard cannula may also be deformed in the elastic range during the piercing process. The hard and soft cannulas may initially be straight and bent during assembly or installation in the cannula holder.

In an alternative embodiment, the cannula unit includes only one soft cannula and one piercing needle, which may be arranged coaxially in the soft cannula and only partially fills the soft cannula in cross section, so that a fluid may still flow through the soft cannula past the piercing needle.

In this case, the soft cannula may include a branch, the piercing needle being withdrawn through a first channel of the soft cannula and the fluid being able to flow through a second channel of the soft cannula to the insertion-side end of the soft cannula. Regardless of the arrangement, the soft cannula may be constructed of a flexible material such as plastic and the hard cannula may be constructed of a rigid material such as steel.

In the present disclosure, a side or direction of the piercing device which points towards the tip of the cannula or the piercing-side end of the cannula may be referred to as "piercing-side" or proximal or as "piercing direction". On the other hand, a side or direction which points towards an end wall of the administration device and which faces away from the piercing site may be referred to as the distal or distal direction. Thus, a single-sided (proximal) area lies opposite a distal area, and a piercing direction (proximal direction) points opposite to a distal direction.

The piercing direction corresponds to the direction in which the cannula unit may be moved during the piercing process. The piercing direction may deviate from the direction in which the cannula tip may be moved for piercing the skin of the user. For example, a single-sided area of the cannula may be deflected between the needle holder and the single-sided end of the cannula, so that the cannula assumes a curved or arched course in the single-sided area. In such a case, the piercing direction of the cannula unit may be different from the direction of movement of the piercing-side region of the cannula.

The cannula unit may be biased in the piercing direction with the biasing or prestressing force. However, a drive element may just as well be biased with the biasing force which, when triggered, may act on the cannula unit and move it in the piercing direction. This drive element may be configured as a separate element and separately from the cannula unit. In both cases, the cannula unit may be moved by the biasing force of the elastic element.

The securing element may hold the biased cannula unit immovably in the securing position, so that the cannula unit may not be moved by the biasing force. The biasing force may be transmitted indirectly from the elastic element to the securing element, such as via a further element such as a transmission element or retaining element or via several such elements. As a result, the securing element may hold the cannula unit in the secured position via one or more elements.

The securing element may deform when heated or may tear apart completely. The material of the securing element may not necessarily have to become liquid or reach its melting point. For example, when the glass transition temperature may be exceeded, a solid amorphous substance or solid glass or polymer changes into a rubbery to viscous state. A softening of the material may suffice for the securing element to be deformed by the biasing force and for the cannula unit to be able to be moved away from the secured position or for the holding function of the securing element to be canceled. The securing element may be softened, weakened, deformed or torn apart at or above a temperature of 80° C. so that the cannula unit may be moved away from the securing position.

In an alternative embodiment, however, the securing element may contract when heated, and the cannula unit may be moved away from the securing position or the holding function of the securing element may be canceled. In this case, the securing element may be formed from a shape-memory polymer, which may contract or shorten when heated.

The term "medicament" or "medicinal substance" in this context may include any flowable medical formulation which may be suitable for controlled administration by means of a cannula or hollow needle, for example a liquid, a solution, a gel or a fine suspension containing one or more medicinal active ingredients.

Thus, a medicament may be a single agent composition or a premixed or co-formulated multiple agent composition from a single container. The term includes drugs such as peptides (e.g. insulins, drugs containing insulin, GLP-1 containing and derived or analogous preparations), proteins and hormones, biologically obtained or active ingredients, active ingredients based on hormones or genes, nutritional formulations, enzymes and other substances both in solid (suspended) or liquid form. The term also includes polysaccharides, vaccines, DNA or RNA or oligonucleotides, antibodies or parts of antibodies as well as suitable basic, auxiliary and carrier substances.

In an embodiment, the piercing device includes a movable retaining element which may be functionally arranged between the cannula unit or the elastic element and the securing element and which may transmit the biasing force from the elastic element to the securing element. "Functional" means that the retaining element may be located in a kinematic chain between the elastic element and the securing element. The retaining element may not necessarily have to be arranged locally or in relation to the structural arrangement between the elastic element and the securing element. Regardless of how the retaining element may be arranged, the retaining element may at least partially transmit the biasing force from the elastic element to the securing element, for instance with the elastic element transmitting the biasing force first to the cannula unit.

The retaining element may be configured in such a way that the retaining element may block the cannula unit in the locking position or prevent it from moving, in that the retaining element may in turn be blocked or prevented from moving by the locking element. The retaining element thus may interact directly with the cannula unit and functions as a connecting element between the cannula unit and the securing element. As a result, the transfer of the biasing force to the securing element may be defined and adjusted by way of the retaining element. A mechanical translation or reduction may therefore be implemented with the retaining element. Depending on the geometric dimensions (lever arm lengths) and the location of the bearing in relation to the location of the force absorption, the preload force may be increased or reduced. The biasing force which acts on the securing element may thus be adjusted with the retaining element, which enables the securing element to be dimensioned in a space-saving manner.

The retaining element may interact with the cannula unit and the securing element via a force-fit or form-fit connection or with a combination of a force-fit and form-fit connection. The retaining element may include a securing surface which may be arranged at an angle to the piercing direction and which interacts with the cannula unit in the securing position and thereby holds the cannula unit in position. The angle at which the securing surface is aligned to the piercing direction may influence the level of force to be transmitted from the biased cannula unit to the securing element. This force may thus be adjusted by selecting the angle. Furthermore, some embodiments, the retaining element may be coupled to the securing element by means of a form-fitting connection.

Alternatively, the piercing device may not have a retaining element and the biasing force may be transmitted directly from the elastic element or from the cannula unit to the securing element. In this case, the cannula unit may interact directly with the securing element without an additional element or component.

The retaining element may be configured as a rotatable lever which may be pivoted about an axis of rotation in order to release the cannula unit from the securing position. The retaining element may be rotatably mounted on the base, a support or holder and may be pivotable relative thereto. With a retaining element as a rotatable lever, the release mechanism may be made compact. The lever may have a securing surface oriented obliquely to the piercing direction at a first end and a coupling element which may be coupled to the securing element at a second end. The securing surface may interact in the securing position with an inclined surface of the cannula unit, so that the cannula unit may be held in position by the retaining element by means of a form fit and may not move.

Alternatively, the retaining element may be configured to be only displaceable or to be both displaceable and rotatable.

The retaining element may be moved for piercing by at least part of the biasing force generated by the elastic element. In some embodiments, the retaining element may only be moved by the biasing force. This means that if the holding function of the securing element may be canceled by heating the securing element, the retaining element may be moved solely by the biasing force. There may therefore be no need for an additional actuator to move the retaining element. This may enable a simple and inexpensive construction.

When triggered, the retaining element may be pressed away from an inclined surface of the cannula unit via its securing surface, as a result of which the retaining element may be moved away from a movement path of the cannula unit. The cannula unit may then move away in the piercing direction in order to carry out the piercing process.

The securing element may include an inclined surface which, in the securing position of the cannula unit, interacts with an opposing surface due to the biasing force in such a way that at least part of the thermosensitive area of the securing element may be pressed against the heating element.

A mating surface may be located on the base, a support or a holder of the heating element or the securing element. The securing element may be mounted movably relative to a holder of the securing element. This means that the securing element may move at least in the range of a few millimeters, such as a few tenths of a millimeter, relative to the holder of the securing element.

The securing element may be pressed with its inclined surface against the mating surface by the elastic element due to the biasing force. As a result, the securing element may slip or slide with its inclined surface on the mating surface, as a result of which the securing element may move minimally, such as less than a millimeter, or less than a tenth of a millimeter, in the direction of the heating element, so that at least part of the thermosensitive area may be pressed against the heating element. This may avoid an air gap or space remaining between the thermosensitive area and the heating element, which may have an insulating effect and could prevent the thermosensitive area from being heated. The inclined surface on the securing element and the counter surface may thus enable efficient heating of the thermosensitive area through heat transfer. The heating of the thermosensitive area may therefore not be carried out by means of convection.

The inclined surface on the securing element may be configured as a ramp which may have an angle of between 60° and 80°, or 70°, with respect to a longitudinal axis of the securing element. The mating surface on the holder may be configured as a ramp with the same angle. Furthermore, in some embodiments, an inclined surface may be present on both longitudinal sides of the securing element, as a result of which the securing element may be moved relative to the holder without rotating or being misaligned.

The securing element may be configured as a separate component from the heating element. The securing element therefore may not include a built-in or integrated heater that serves as a heating element. In contrast, the heating element may be configured as a separate component separate from the securing element or may be integrated in a separate component. This may allow the heating element to be installed and replaced quickly. The securing element may be formed from an amorphous plastic such as polystyrene, polyvinyl chloride or polycarbonate. The securing element may be formed mainly from acrylonitrile butadiene styrene ABS, a polycarbonate (PC)-ABS polymer blend or a glass fiber reinforced ABS. Due to the thermal properties of amorphous plastics, the securing element may be heated efficiently.

In an alternative embodiment, the heating element may be integrated into the securing element. A potential disadvantage of this configuration may be that the integrated heating element may be damaged if the securing element begins to deform due to the heat of the heating element. There may then be the risk that the damaged heating element may no longer heat the securing element sufficiently, so that the securing element may not deform sufficiently and, as a result, the triggering of the cannula unit may not function correctly.

In some embodiments, the heating element may be integrated into a printed circuit board and the heating element may be implemented as an electrical resistor. If energized, the resistor may heat up and may heat the thermosensitive area of the securing element. The heating element may be configured to be flat. The heating element may include an area between 1 mm$^2$ and 2.5 mm$^2$ and a thickness between 10 and 50 m.

In some embodiments, the heating element may be formed from a polymer paste (carbon conductive composition) which, together with the conductor track geometry of the circuit board, may result in a specific electrical resistance. The resistance may be between 10 and 40 ohms and the heat output achieved may be between 200 and 700 mW.

Alternatively, the heating element may be configured, for example, as a heating wire or heating coil.

The securing element may have an elongated shape with a taper in the thermosensitive area and may be arranged such that the taper and the heating element at least partially overlap. The securing element may thus be heated or melted by the heating element in the region of the taper. The securing may have a smaller cross-sectional area in the area of the taper compared to the rest of the area. This may allow the thermosensitive area to be heated or melted quickly and efficiently. The securing element may rest with a surface in the region of the taper on a surface of the heating element, so that the heat transfer from the heating element to the securing element may take place efficiently.

In some embodiments, the cannula unit may include a first and a second cannula, the second cannula may be acted upon by a second biasing force from a second elastic element counter to the piercing direction. The first cannula may be constructed of a flexible material such as a flexible plastic and the second cannula may be constructed of a material that may be more rigid than the flexible material, such as steel. The flexible plastic of the first cannula may for example be a fluoropolymer such as FEP. The first cannula may be referred to as a soft cannula and the second cannula may be referred to as a hard cannula. In some embodiments, however, the stiffer or more rigid material may still be bent so that the first and second cannulas may be deflected. The first elastic element may serve to move the cannula unit including the first and second cannula for a piercing movement with the cannula, while the second elastic element may serve to withdraw the second cannula from the skin after piercing the skin.

The more rigid cannula may be arranged coaxially with the flexible cannula and may be located within the flexible cannula.

In an alternative embodiment, however, the flexible cannula may be placed inside the more rigid cannula.

In some embodiments, the rigid and flexible cannula may be pierced together into the skin with the biasing force of the first elastic element and the rigid cannula may then be withdrawn again with the biasing force of the second elastic element, while the flexible cannula remains in the skin. The flexible cannula may be held in position by a remaining force of the first elastic element. Alternatively, the cannula holder of the flexible cannula may be held in position by means of an anchor to the support or base. A fluid may then, for example, enter from a reservoir through a distal end of the rigid cannula and flow through the rigid cannula into the flexible cannula and from there into the body of the user.

Alternatively, however, only a single cannula may be inserted into the skin of the user during the piercing process.

In this case, the single cannula may at least partially be constructed of a rigid material in order to enable rapid insertion. The cannula unit with the first and second cannula and the second elastic element may be moved from the secured position into a piercing position and the second cannula may be moved away from the piercing position again by the second biasing force, the first cannula remaining in the piercing position. The cannula unit may be moved in the piercing direction from the secured position into the piercing position, while at least one area of the cannula may not necessarily be required to be moved into the piercing position. As stated above, the cannula may be deflected or bent. In this case, the cannula tip may move in a different direction than the other elements of the cannula unit during the piercing process.

In some embodiments, the first and the second elastic element may be arranged coaxially to one another. For example, the first elastic element, which may move the entire cannula unit with the first and second cannula in one piercing direction through its biasing force or biasing energy, may be arranged within the second elastic element, which may move the second cannula counter to the piercing direction. However, in an alternative embodiment, the first and the second elastic element may also be arranged interchanged. Such an arrangement may allow a compact construction of the piercing device. Alternatively, the elastic elements may also be arranged one behind the other or next to one another. The first and second elastic element may be configured, for example, as a mechanical spiral spring or as a hollow cylindrical elastomer element.

In addition, one of the two elastic elements may be arranged in the longitudinal direction of the elastic elements at least partially within the other of the two elastic elements, for instance concentrically. The elastic elements may therefore not be arranged one behind the other in the longitudinal direction or in the axial direction, but may be arranged one inside the other. As a result, the piercing device may be configured to be compact in relation to the longitudinal direction.

The first elastic element and the second elastic element may be each configured as a mechanical spring, such as a spiral spring. With a mechanical spring, such as in the form of a compression or tension spring, its compression and expansion may enable a biasing force to be generated in a simple manner, and the biasing force may be achieved by compressing the spring. In an alternative embodiment, the elastic elements may also be implemented in the form of elastomer elements.

The piercing device may include a position detector or position sensor, and the position detector may determine whether the cannula unit has moved away from the secured position or whether the cannula unit may be in the piercing position. The position detector may be actuated via a cannula holder of the cannula unit. The cannula holder may have a contact surface in the form of a bevel, by means of which a movable element of the position detector may be adjusted in the piercing position, whereby a sensor signal may be generated. The cannula holder may thus serve as a trigger element for the position detector.

The cannula holder may be configured to hold the cannula immovably. The cannula holder may be movable, e.g., displaceable, together with the cannula, relative to the base, a support or holder.

Implementations of the present disclosure further relate to an administration device, such as an infusion pump, including a disposable unit and a reusable unit that may be coupled to the disposable unit. The reusable unit may include a drive unit and the disposable unit may include a reservoir for receiving a medical substance and a piercing device as described above, which may be in fluid connection with the reservoir. The disposable unit may be for single use. This means that the disposable unit may be detached from the reusable unit and disposed of after a certain time or when all the medical substance has been administered. The reusable unit may be used several times and may be coupled again with a newly inserted disposable unit.

In some embodiments, the administration device may be configured as a patch pump. A patch pump may be an infusion pump in which the infusion set and the actual pump with the entire mechanism may be combined in a common housing. The patch pump may be adhered directly onto the user's skin. The patch pump may be set and controlled via a mobile control device, such as a "Personal Diabetes Manager" (PDM) or an application on a mobile phone, which may communicate wirelessly with the patch pump. The housing of the patch pump may be configured in two parts, with a disposable unit described herein and a reusable unit.

BRIEF DESCRIPTION OF THE DRAWINGS

In connection with the figures, various embodiments of the present disclosure are described below. These are intended to show implementations of the present disclosure and are in no way to be interpreted as restrictive.

DETAILED DESCRIPTION

Figure 1:
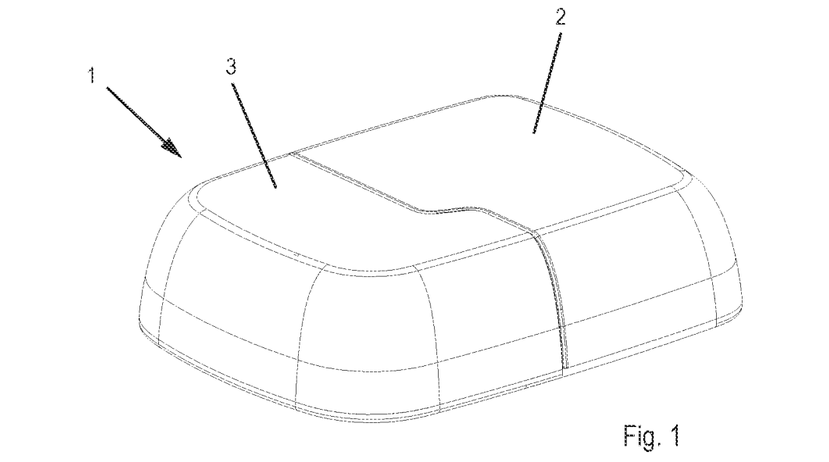
FIG. 1 shows a perspective view of a patch pump, which includes a disposable unit and a reusable unit, according to implementations of the present disclosure.

FIG. 1 shows a perspective view of an administration device in the form of a patch pump 1 which includes a piercing device 10 according to implementations of the present disclosure. The patch pump includes a disposable unit 2, and a reusable unit 3.

Figure 2:
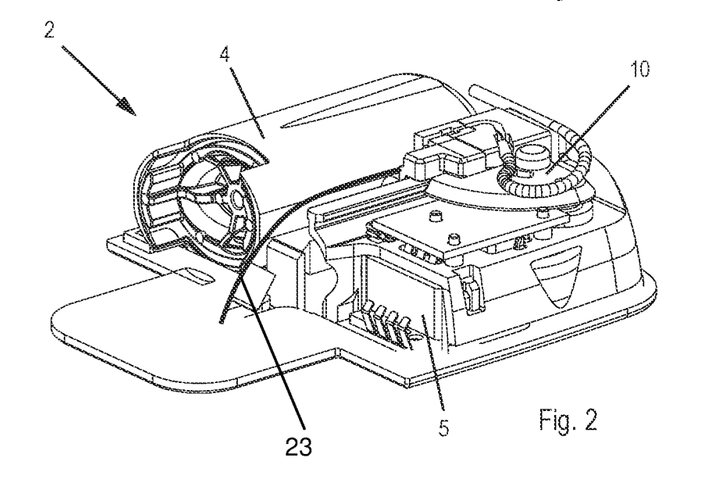
FIG. 2 shows a perspective view of the disposable unit of the patch pump, with the disposable part including a piercing device, according to implementations of the present disclosure.

In FIG. 2, the disposable unit 2 is shown in perspective without the housing of the patch pump 1. The disposable unit 2 contains a reservoir 4 that may be filled with a medical substance, a power supply unit 5 with a disposable battery in the form of a button battery, an adhesive surface for attaching the patch pump 1 to the user's skin, and a piercing device 10 according to implementations of the present disclosure.

The reusable unit 3 may be detachably and sealingly coupled to the disposable unit 2 via a bayonet lock and includes a drive unit for driving a piston rod, an encoder, a rechargeable battery and control electronics. When the disposable unit 2 and reusable unit 3 are electrically coupled to one another, the battery may be charged by the disposable battery in disposable unit 2. The battery may be used to power the motor contained in the reusable unit 3 and the control electronics. This may be used to control the motor and may transfer data to an external control unit, e.g., exchange via a radio link. The motor may act mechanically on the reservoir in the disposable unit 2 via the piston rod in order to dispense the medical substance contained therein. The battery may also supply the electrical energy for triggering the piercing process as described herein.

Figure 3:
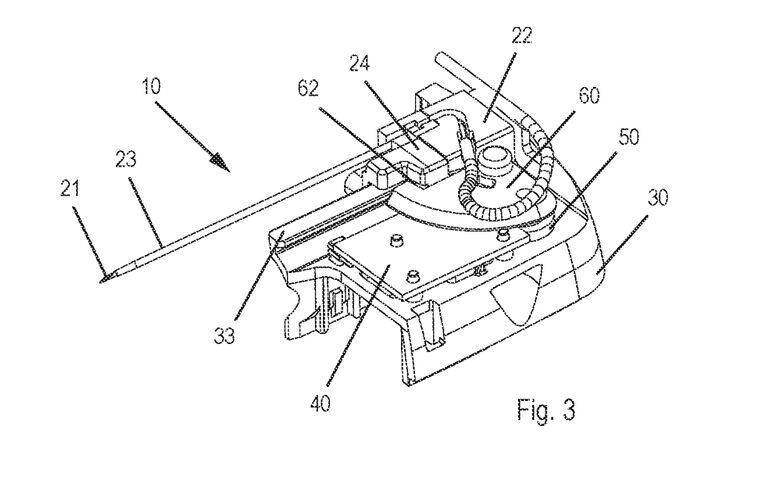
FIG. 3 shows a piercing device according to implementations of the present disclosure.
Figure 4:
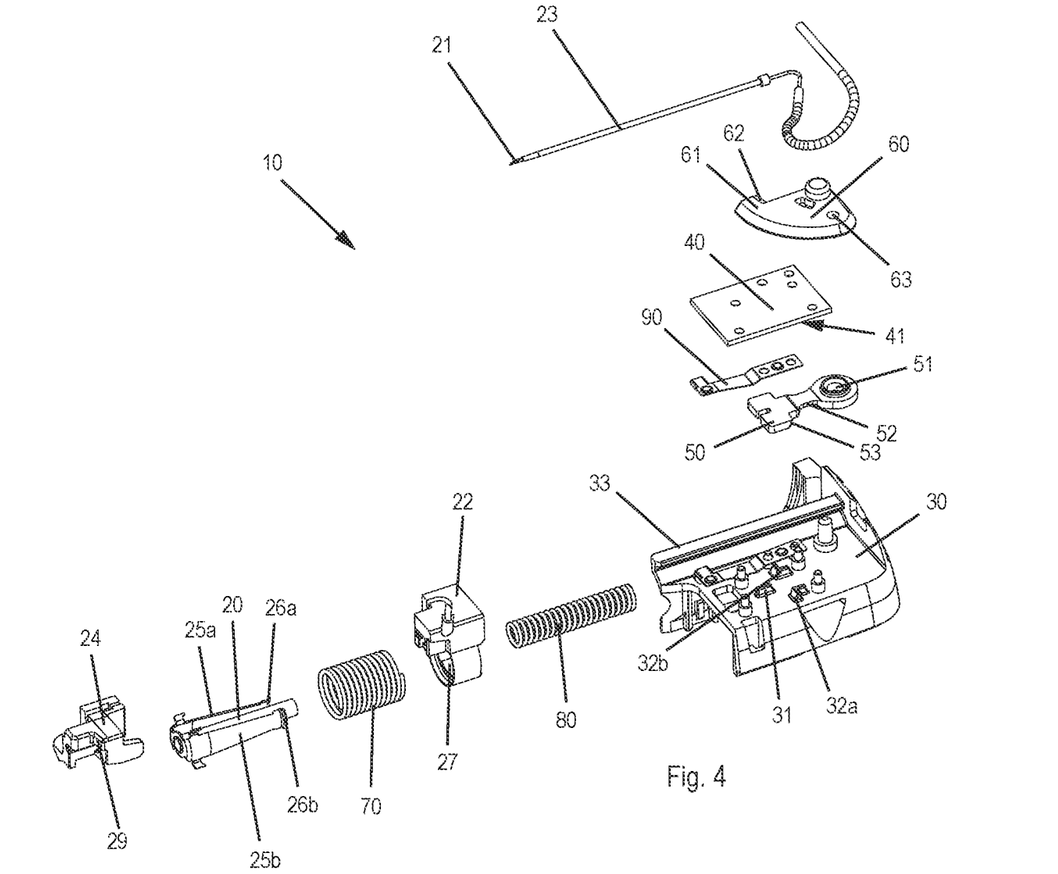
FIG. 4 shows an exploded view of the piercing device of FIG. 3.

The components of the piercing device 10 are explained below with reference to FIGS. 3 and 4. FIG. 3 shows a perspective view of the piercing device 10 according to implementations of the present disclosure. FIG. 3 shows a hard and soft cannula 21, 23 in an initial state before assembly, in which the cannulas are not bent. As shown in FIG. 2, the hard and soft cannulas 21, 23 are bent in the assembled state, with the soft cannula 23 visible. FIG. 4 shows an exploded view of the piercing device 10.

The piercing device 10 includes a cannula unit containing a guide cylinder 20 with two lateral arms 25a, 25b, the hard cannula 21, the soft cannula 23 and a hard cannula holder 22 and a soft cannula holder 24, which hold the hard or soft cannula 21, 23 and are able to move it relative to a base 30 or support. The arms 25a, 25b of the guide cylinder 20 are connected to the guide cylinder 20 at a proximal end thereof. The arms 25a, 25b run along a longitudinal axis of the guide cylinder 20 and may be moved in a distal area in the radial direction with respect to the guide cylinder 20. At the distal end of the arms 25a, 25b, they each have a tab 26a, 26b pointing radially outward, as shown in FIG. 4. The piercing device 10 also includes an elastic element configured as a piercing spring 80 in the form of a compression spring, with which the cannula unit may be acted upon in a piercing direction by a biasing force; a second elastic element configured as a return spring 70 may also be configured as a compression spring; the base 30; a printed circuit board 40 fastened on the base 30; a securing element 50 arranged between the base 30 and the circuit board 40; and a retaining element 60, which may be connected to the securing element 50, may transmit the biasing force to the securing element 50 and hold the cannula unit acted upon by force in a securing position. A position detector 90 in the form of a shaped sheet metal strip may be also arranged on the base 30.

In the embodiment shown, the piercing device 10 may be configured as a cannula piercing and retraction mechanism and, after being triggered by the piercing spring 80, may automatically push out the hard cannula 21 together with the soft cannula 23 surrounding the hard cannula 21 and, after the pushing-out process, withdraw the hard cannula 21 from the inside of the soft cannula 23 by the return spring 70. The extended soft cannula 23 remains in the extended state. If hard and soft cannulas 21, 23 are applied to a body of the user before being pushed out (e.g., triggered), an automatic piercing and body insertion process may thus be implemented.

Figure 5:
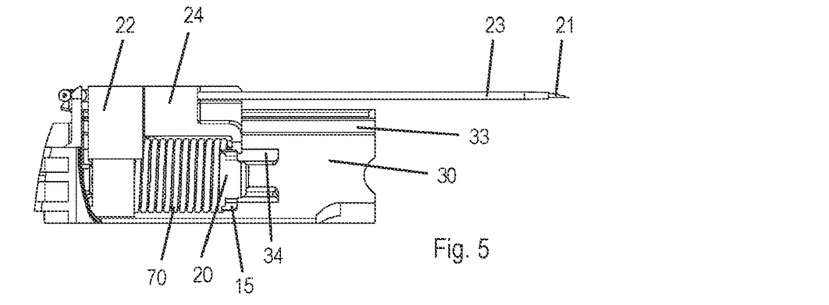
FIG. 5 shows a side view of the piercing device in which the piercing unit is in a secured position, according to implementations of the present disclosure.
Figure 6:
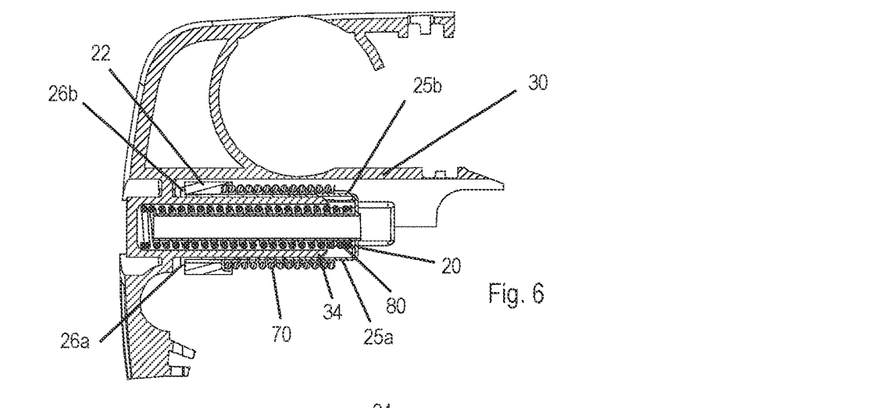
FIG. 6 shows a sectional view of the piercing device in the secured position of FIG. 5, the section running horizontally through the piercing device.

FIGS. 5 and 6 show the piercing device 10 in a secured position of the piercing unit. FIG. 5 is a side view of the piercing device 10, and FIG. 6 is a sectional view of the piercing device 10, with the cross-section running horizontally through the piercing device 10 and through a central axis of the piercing spring 80 and the return spring 70.

The soft cannula 23 may be arranged coaxially and sealingly over the hard cannula 21. In the secured position of the cannula unit, a sharpened tip of the hard cannula 21 may protrude a few millimeters from the soft cannula 23 and may enable the skin to be pierced as smoothly and painlessly as possible. The inner circumference of the soft cannula 23 may rest sealingly on the outer circumference of the hard cannula 21 so that no liquid may pass through the area where the hard cannula 21 and the soft cannula 23 are in contact. The hard cannula 21 may be displaced within the soft cannula 23. The soft cannula 23 may be constructed of a flexible plastic such as a fluoropolymer such as FEP, while the hard cannula 21 may be more rigid and may be constructed of steel. The soft and hard cannulas 21, 23 may each be bendable and may be bent or curved in their longitudinal direction.

The soft cannula 23 may be held immovably on the soft cannula holder 24 by means of a form-fitting connection. For this purpose, the soft cannula holder 24 may have an upwardly open channel in which the hard and soft cannulas 21, 23 may be inserted. At the upper end, the channel walls may have projections pointing toward the center of the channel, so that the hard and soft cannulas 21, 23 may not move upwards out of the channel. The soft cannula 23 may also have over a section a thickening which fits into a correspondingly shaped channel section. As a result, the soft cannula 21 may be held in a form-fitting manner in the longitudinal direction in the channel of the soft cannula holder 24. The soft cannula holder 24 may be displaced together with the soft cannula 23 relative to the base 30 on a guide 33 of the base 30 along a longitudinal direction of the base 30. The guide 33 may be T-shaped in cross section and the soft cannula holder 24 may have a corresponding T-shaped opening with which the guide 33 may be held and guided on.

As shown in FIG. 3, in the secured position of the cannula unit, the hard cannula holder 22 may be located on the distal (not the penetration-side) end of the soft cannula holder 24, and the hard cannula holder 22 may hold the hard cannula 21 immovably via a form-fitting connection. For this purpose, the hard cannula holder 22 may have an upwardly open, curved channel in which the hard cannula 21 may be inserted. As in the case of the soft cannula holder 24, projections in the channel of the hard cannula holder 22 may prevent the hard cannula 21 from moving upwards and may thereby hold the hard cannula 21 in the channel. Due to the arched shape of the channel, the hard cannula 21 may also be held in the hard cannula holder 22 in a form-fitting manner in the longitudinal direction. The hard cannula holder 22 may be guided displaceably via a T-shaped opening on the guide 33 of the base 30. In addition, the hard cannula holder 22 may surround a horizontal, cylindrical mandrel 34 (FIG. 5) of the base 30 by means of a circular opening 27. The mandrel 34 may be connected to the base 30 at one end and may be free at the other end. This horizontal mandrel 34 may support the guide cylinder 20 such that the guide cylinder 20 may be displaced in the longitudinal direction. The mandrel 34 may have a horizontal bore (FIG. 6) in which the piercing spring 80 may be located. The piercing spring 80 may be supported at the distal end on the base of the bore and at the insertion-side end on a proximal end wall of the guide cylinder 20, shown in FIG. 6.

The return spring 70 may be arranged around the guide cylinder 20, the circumferential wall of which may surrounds the mandrel 34. As shown in FIG. 6, the return spring 70 may strike with its distal end on the hard cannula holder 22 and may be supported with its proximal or penetration-side end on radial projections 15 of the guide cylinder 20 (FIG. 5). The return spring 70 may thus be positioned coaxially and, viewed in the longitudinal direction, overlapping with the piercing spring 80. The return spring 70 may be compressed in the secured position.

The piercing spring 80 may also compressed in the secured position, as shown in FIG. 6, and may thereby generate a biasing force which acts on the guide cylinder 20. The guide cylinder 20 may transmit the biasing force to the hard cannula holder 22 by means of its arms 25a, 25b and further via the tabs 26a, 26b of the arms. The hard cannula holder 22 rests with a proximal surface on the soft cannula holder 24, whereby the biasing force may be transmitted to the soft cannula holder 24. The soft cannula holder 24 may in turn be supported on a nose 61 of the retaining element 60.

Thus, the entire cannula unit to which the biasing force is applied may be prevented from moving in the piercing direction by the retaining element 60. For this purpose, the soft cannula holder 24 may have a contact surface 29, shown in FIG. 4, which may be oriented obliquely to the longitudinal axis of the cannulas or obliquely to the direction of movement of the soft cannula holder 24. In the secured position, the contact surface 29 may strike a securing surface 62 of the protruding nose 61 of the retaining element 60. The retaining element 60 may have the shape of a circular segment of slightly less than 90° and may be rotatably mounted on the base 30 and on a housing of the patch pump 1. The retaining element 60 may be pivoted by approximately 12° relative to the base 30. The nose 61 may be arranged on one side of the circular sector and a pin 63 may be arranged on an opposite side of the circular sector. As explained herein, the retaining element 60 may act as a lever.

In the secured position of the cannula unit, the retaining element 60 with its nose 61 may hold the cannula unit, which may be subjected to the biasing force, in a distal position via the securing surface 62. The biasing force which acts on the retaining element 60 via the cannula unit, the retaining element 60 may transfer at least partially to the securing element 50, which may hold the retaining element 60 in position and prevent the retaining element 60 from rotating. For this purpose, the pin 63 of the retaining element 60 may engage in a circular opening 51 in the securing element 50, see FIGS. 3 and 4. As a result, the securing element 50 may block the retaining element 60 and thus hold the entire cannula unit in position. In other words, the retaining element 60 may transmit the biasing force generated by the compressed piercing spring 80 partly to the securing element 50 and partly to the base 30.

The securing element 50 may have an elongated shape and may be constructed of amorphous plastic. At a piercing-side or proximal end, the securing element 50 may have a horizontally continuous groove. A cam 31 of the base 30 engages in this groove and thereby supports the securing element 50 in the proximal direction. In addition, the securing element 50 may be secured against rotation by the groove and the cam 31. As explained in detail further herein, the securing element 50 may have an inclined surface 53 on each side, which may rest on opposite surfaces 32a, 32b of the base 30 and may thereby prevent the securing element 50 from moving in the distal direction.

The circular opening 51 of the securing element 50, which receives the pin 63 of the retaining element 60, may be located at the distal end of the securing element 50. In the middle between the two ends, the securing element 50 may have a taper 52 which, compared to the other regions of the securing element, may have a smaller cross-sectional area.

This area with the taper 52 may be heated when triggered, as described herein. The taper 52 may therefore also be referred to as a thermosensitive area.

A printed circuit board 40 (PCB) may be attached to the base 30 by hot caulking on bases of the base 30 and above the securing element 50. The circuit board 40 may have a planar heating element 41 which may be integrated into the circuit board 40. The heating element 41 may be implemented as an electrical resistor and may be formed from a polymer paste. The heating element 41 may have an area of approximately 2 mm² and a thickness of approximately 20 μm. Depending on the configuration, the electrical resistance may be between 10 and 30 ohms, with an achievable thermal output of around 300 to 650 mW.

As shown in FIG. 3, the securing element 50 may be placed between a surface of the base 30 and an underside of the circuit board 40. The circuit board 40 and securing element 50 may be arranged in such a way that the area with the taper 52 may be located directly below the heating element 41 of the circuit board 40.

The inclined surfaces 53 of the securing element 50 may be at an angle of approximately 20 degrees to the perpendicular direction, as shown in FIG. 4. The mating surfaces 32a, 32b of the base 30 may have the same angle. In the secured position, the transmitted biasing force may pull the securing element 50 with its inclined surfaces 53 against the mating surfaces 32a, 32b of the base 30, so that the inclined surfaces 53 of the securing element 50 easily slip or slide upwards on the mating surfaces 32a, 32b away from the base 30. As a result, the securing element 50 may be pressed against the circuit board 40 and at the same time may be held against a distal movement. The taper 52 of the securing element 50 may thereby be pressed onto the heating element 41 in the circuit board 40. An air gap between the taper 52 and the heating element 41 may thus be effectively avoided.

In the secured position, an area of the position detector 90 may rest on the printed circuit board 40, as a result of which contact may be established between the sheet metal of the position detector 90 and a printed circuit board contact surface. The control of the patch pump 1 may receive a signal that the cannula unit is in the safety position.

In order to trigger the piercing process, so that the hard and soft cannula 21, 23 are moved in the piercing direction for piercing, the heating element 41 may be supplied with power via the control of the patch pump 1. The heating element 41 may be heated by the electrical resistance. As a result of this heating, the taper 52 of the securing element 50 may be heated to approx. 100° C., and the amorphous plastic of the securing element may begin to deform. As a result of the biasing force generated by the piercing spring 80, the heated taper 52 may be stretched or the securing element 50 tears apart at the point of the taper 52. As a result, the retaining element 60 may no longer be blocked by the securing element 50, the biased piercing spring 80 may relax as a result and may move the cannula unit in the piercing direction. During this movement, the cannula unit may press or urge away the nose 61 of the retaining element 60 via its contact surface 29, which may be arranged obliquely to the direction of movement, so that the retaining element 60 may pivot about its axis of rotation. The piercing spring 80 may relax further and may thereby displace the cannula unit including the hard and soft cannulas 21, 23, the hard and soft cannula holder 22, 24, the guide cylinder 20 and the biased return spring 70 in the piercing direction. The hard and soft cannulas 21, 23 may therefore be moved towards the injection site at the same time.

Figure 7:
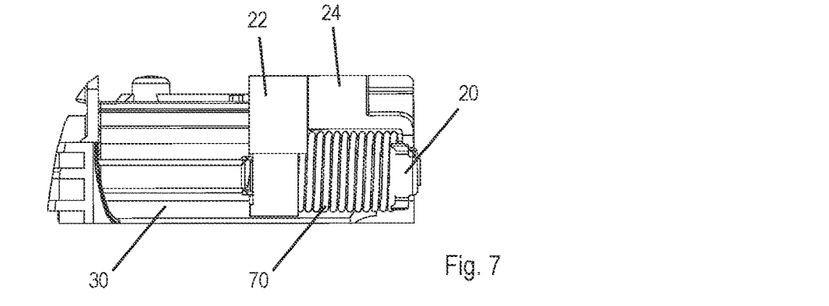
FIG. 7 shows a side view of the piercing device in which the piercing unit is in a piercing position, according to implementations of the present disclosure.
Figure 8:
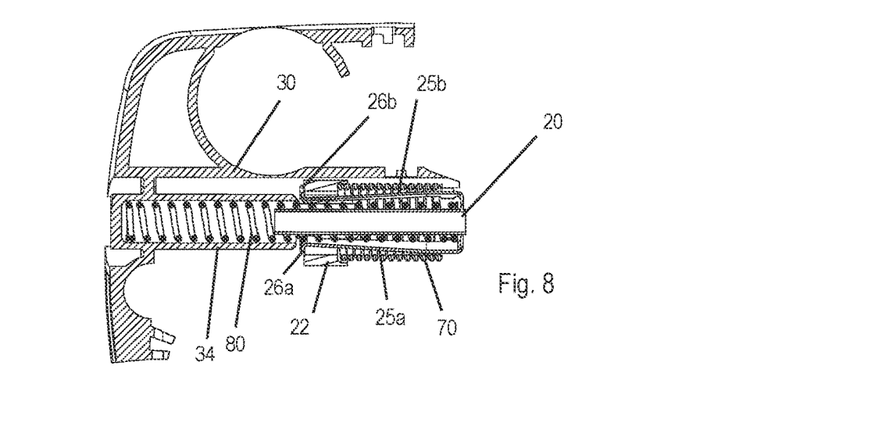
FIG. 8 shows a sectional view of the piercing device in the piercing position of FIG. 7, the section running horizontally through the piercing device.

The cannula unit may be moved up to a stop at which point the cannula unit may be in a piercing position. FIGS. 7 and 8 show the cannula unit in this piercing position, FIG. 7 showing a side view in which the hard and soft cannulas 21, 23 are not shown. FIG. 8 is a sectional view in which the cross-section runs horizontally and through the central axes of the piercing spring 80 and the return spring 70 through the piercing device 10.

In the piercing position, a single-sided end of the sheet metal of the position detector 90 may be deflected by a bevel on the soft cannula holder so that the sheet metal of the position detector 90 no longer has any contact with the contact surface on the circuit board. This may open a contact switch. The controller of the patch pump 1 may interpret this as a signal that the cannula unit is in the piercing position.

Figure 9:
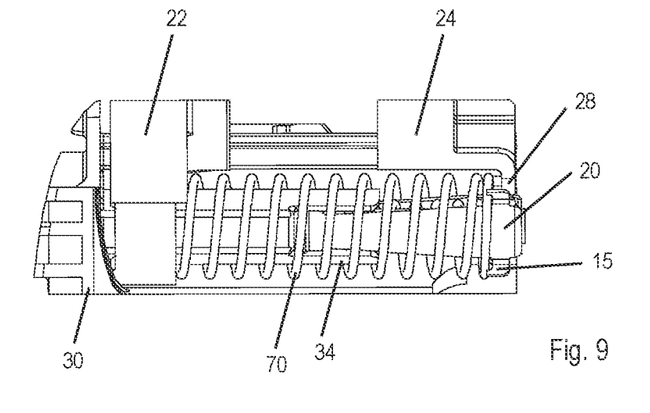
FIG. 9 shows a side view in which the piercing unit is in a retracted position.
Figure 10:
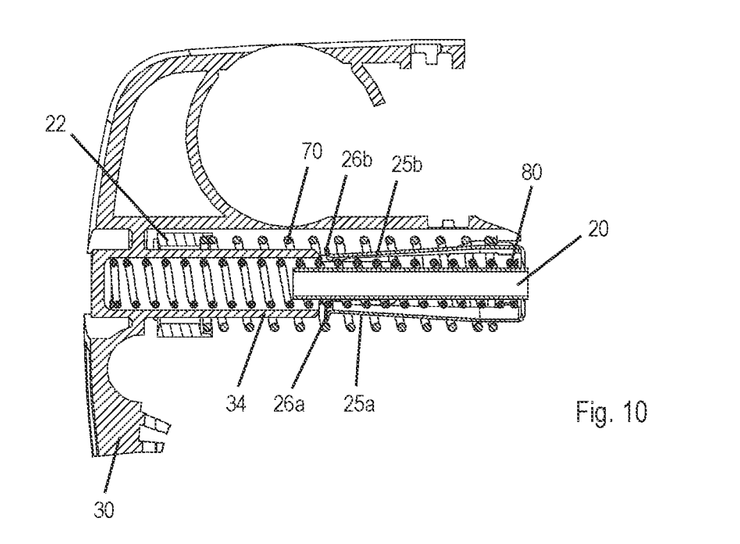
FIG. 10 shows a sectional view in which the piercing unit is in the retracted position of FIG. 10, the section running horizontally through the piercing device.

During the displacement in the piercing direction, the movable lateral arms 25a, 25b of the guide cylinder 20 may be guided along the mandrel 34 of the base 30. However, in the area in which the arms 25a, 25b rest on the mandrel 34, the mandrel 34 may be slightly shorter than the displacement path of the cannula unit, so that the arms 25a, 25b of the guide cylinder 20, which are biased radially inward, at the end before the cannula unit stops in the area of the mandrel 34 may slide and move radially inward. The deflection of the arms 25a, 25b may be supported by the spring forces of the piercing spring 80 as well as the return spring 70. As a result of the sliding, the tabs 26a, 26b of the arms 25a, 25b may also be moved radially inward (FIGS. 8 and 10), as a result of which the hard cannula holder 22 may be released from the guide cylinder 20. The return spring 70 may relax as a result and may move the hard cannula holder 22 in the distal direction back into the distal starting position, whereby the hard cannula 21 connected to the hard cannula holder 22 may be withdrawn from the soft cannula 23, so that only the soft cannula 23 remains in the extended state. This retraction position of the cannula unit is shown in FIGS. 9 and 10. FIG. 9 shows a side view in which the hard and soft cannulas 21, 23 are not shown, while FIG. 10 shows a sectional view with a cross-section running horizontally through the piercing device 10.

As shown in FIGS. 9 and 10, the return spring 70 has relaxed and has thereby pushed the hard cannula holder 22 together with the hard cannula 21 back into the initial, distal position. In this retraction position, the return spring 70 may be supported at the distal end on the retracted hard cannula holder 22 and at the proximal end on the projections 15 of the guide cylinder 20. At the proximal end of the return spring 70, the soft cannula holder 24 may rest with its stop 28 on the return spring 70. As a result, the return spring 70 may hold the soft cannula holder 24 with the soft cannula 23 in the proximal piercing position. The guide cylinder 20 may be held in the proximal piercing position by the relaxed piercing spring 80. In an alternative embodiment, the relaxed piercing spring 80 may hold the soft cannula holder 24 with the soft cannula 23 in the piercing position.

Figure 11:
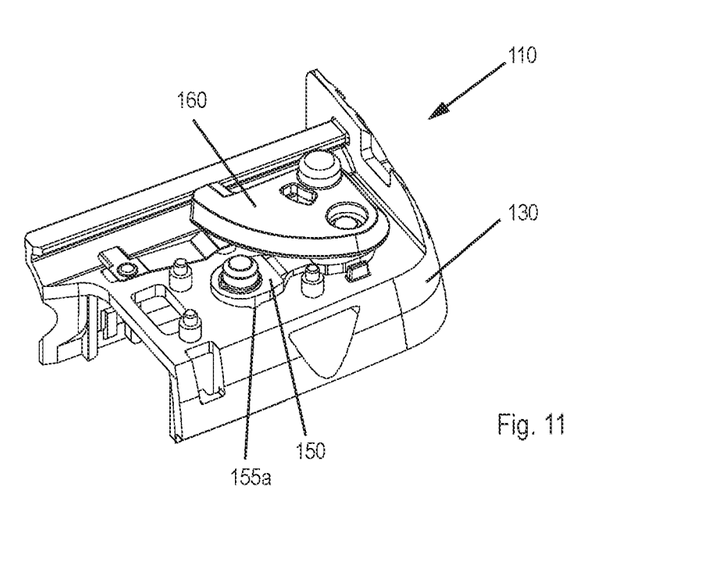
FIG. 11 shows a perspective view of a further embodiment of a piercing device with a base having bearing pins, according to implementations of the present disclosure.

FIG. 11 shows a perspective view of a further embodiment of a piercing device 110 according to the implementations of the present disclosure. The base 130 with the securing element 150 and the retaining element 160 shown in FIG. 11. In contrast, the position detector, the cannulas and the cannula holder are not shown for the sake of clarity.

In contrast to the embodiment described in connection with FIGS. 2-10, the securing element 150 may be mounted and held on the base 130 in a different way. In addition, as described in detail herein, the securing element 150 and retaining element 160 have a different shape than in the embodiment according to FIGS. 2-10.

Figure 12:
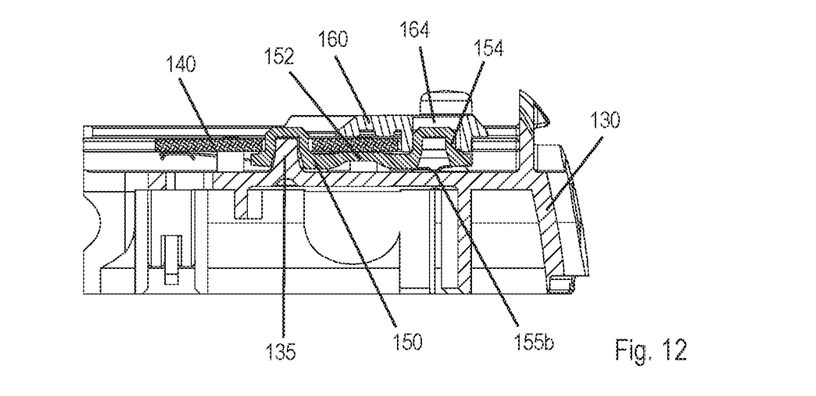
FIG. 12 shows a sectional view of the embodiment of FIG. 11.

FIG. 12 shows a sectional view of the embodiment according to FIG. 11, the cross-sectional plane running vertically through the printed circuit board 140, the securing element 150, the base 130, and through the central axis of a conical bearing pin 135 of the base 130.

In FIG. 12, the securing element 150 rests on the one hand on the conical bearing pin 135 of the base 130 and may thus be held at this point on the base 130 and on the other hand engages an opening 164 in the retaining element 160 with an end that may be freely movable relative to the base 130. For this purpose, the securing element 150 may have a truncated conical pin 154 which may be inserted into the circular opening 164 in the retaining element 160. On the underside, the securing element 150 may have, in its proximal and distal area, a web 155a, 155b each running across the underside of the securing element 150. The proximal web 155a shown in FIG. 11, and the distal web 155b in FIG. 12. With these webs 155a, 155b, the securing element 150 may rest on a surface of the base 130.

The printed circuit board 140, which may be located above the securing element 150, may have a circular recess or hole through which the bearing pin 135 and the area of the securing element 150 resting on it protrude, as shown in FIG. 12.

As a result of the at least partially transmitted biasing force from the piercing spring 80 to the securing element 150 and the geometric shape of the securing element 150, the securing element 150 may be deliberately deformed. The introduction of force from the retaining element 160 to the securing element 150 takes place on the taper 152, for instance, viewed in the vertical direction, above an unsupported area or neutral fiber in the longitudinal cross section of the taper 152 of the securing element 150. This creates a torque which causes the securing element 150 to bend upward. The taper 152 of the securing element 150 may thereby be pressed upwards against an underside of the circuit board 140. When the heating element heats up, the securing element 150 may be weakened or melted in the region of its taper 152, so that the retaining element 160 acted upon by the biasing force may rotate and thereby, as described above, the piercing process may be triggered. Since the securing element 150 may be rotatably mounted on the base 130, it may also rotate slightly during the movement of the retaining element 160, as a result of which the taper 152 may be pressed evenly onto the heating element. This enables optimal heat transfer from the heating element to the securing element 150.

Figure 13:
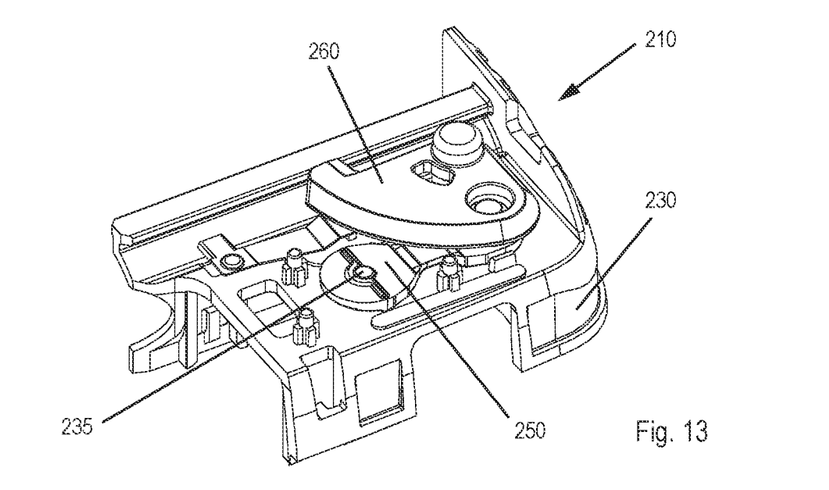
FIG. 13 shows a perspective view of a further embodiment of a piercing device with a securing element with an opening for receiving a bearing pin of a support, according to implementations of the present disclosure.
Figure 14:
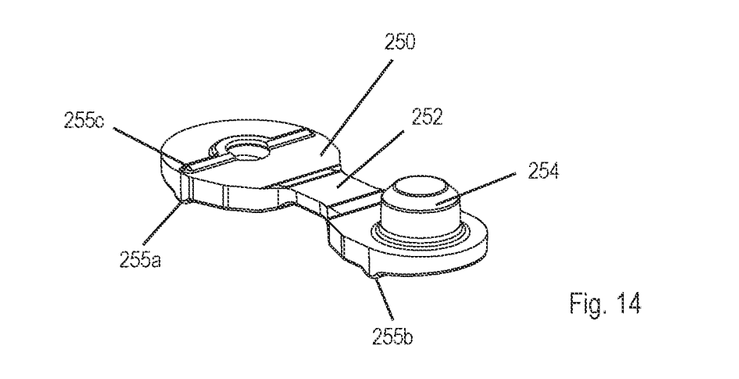
FIG. 14 shows a perspective view of the securing element of the embodiment of FIG. 13.
Figure 15:
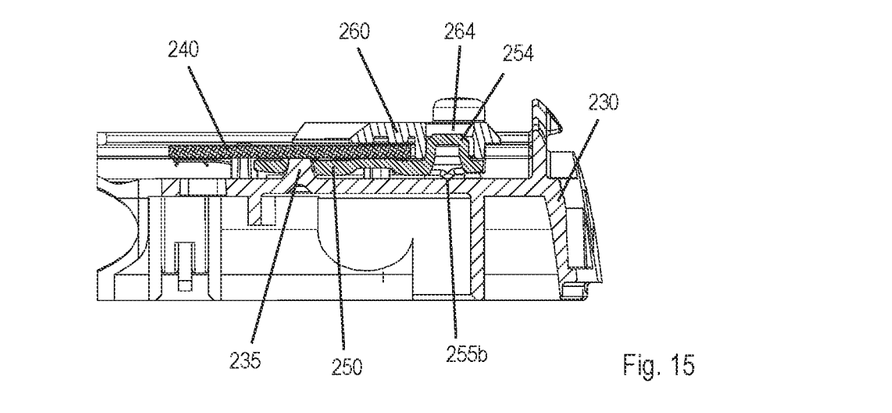
FIG. 15 shows a sectional view of the embodiment of FIG. 13.

A further embodiment of the piercing device 210 according to implementations of the present disclosure is shown in FIGS. 13 to 15. The position detector, the cannulas and the cannula holder are not shown in FIG. 13 for the sake of clarity. In contrast to the embodiment shown in FIGS. 11 and 12, the bearing pin 235 in the embodiment according to FIGS. 13 to 15 may be smaller and the securing element 250 defines an opening which receives the bearing pin 235. As a result, the securing element 250 may be held on the base 230. Thus, no opening may be required in the printed circuit board 240, which may simplify its manufacture.

In FIG. 14, the securing element 250 of this embodiment is shown individually and somewhat larger in a perspective view. As shown in FIG. 14, the securing element 250 includes on its underside in the proximal and distal area webs 255a, 255b each with a semicircular cross-section, with which the securing element 250 rests on the surface of the base 230. Compared to the printed circuit board 240 arranged above the securing element 250, the securing element may be supported with a web 255c located on its top surface. In addition, as shown in FIG. 14 both the width and the thickness of the securing element 250 may be reduced in the region of the taper 252 located between the opening and the pin 254.

The piercing device 210 is shown in a sectional view in FIG. 15. As shown, the securing element 250 may be held with one end on the bearing pin 235, e.g., via the opening of the securing element 250, and with the other end, which may be freely movable with respect to the base 230, with the pin 254 arranged in the opening 264 of the retaining element 260.

Figure 16:
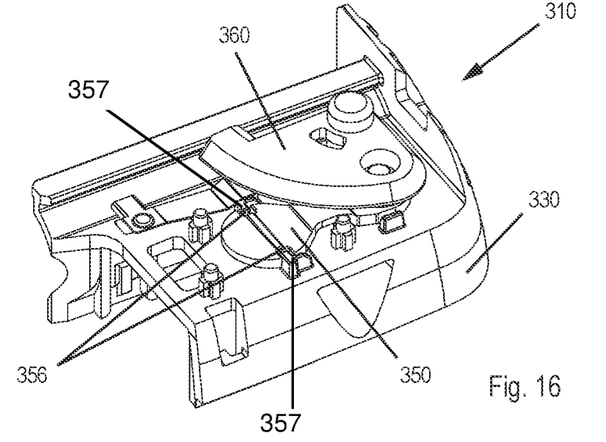
FIG. 16 shows a perspective view of a further embodiment of a piercing device with a support with webs for holding the securing element, according to implementations of the present disclosure.
Figure 17:
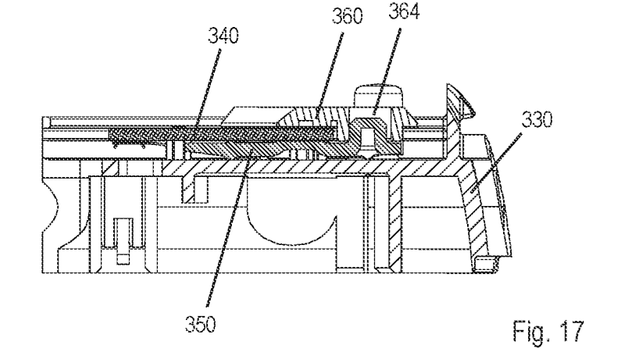
FIG. 17 shows a sectional view of the embodiment of FIG. 16.

FIGS. 16 and 17 show another embodiment of the piercing device 310 according to the implementations of the present disclosure, in which the securing element 350 may include a vertical groove 356 at one end on both sides. One web 357 of the base 330 each protrudes into a groove 356. As a result, the securing element 350 may be held immovable relative to the base 330 in directions parallel to the surface of the base 330. The securing element 350 may be held with its other end free from the base 330 in the opening 364 of the retaining element 360, as described in the previous embodiments according to FIGS. 11 to 15. In the embodiment according to FIGS. 16 and 17, as in the embodiment according to FIGS. 14 and 15, no recess or hole in the circuit board 340 may be necessary due to the two grooves 356 preventing securing element 350 from rotating relative to the base 330.

Figure 18:
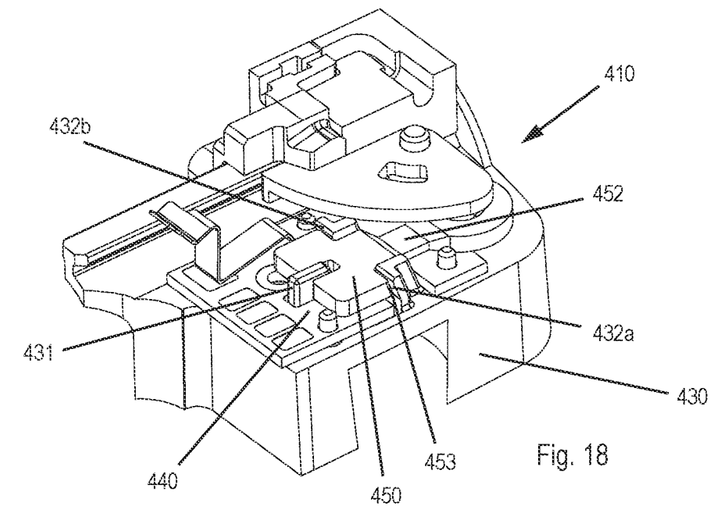
FIG. 18 shows a perspective view of a further embodiment of a piercing device in which the securing element is arranged over the circuit board, according to implementations of the present disclosure.

In a further embodiment of the piercing device 410 according to the implementations of the present disclosure, shown in FIG. 18, in contrast to the embodiments shown in FIGS. 1 to 17, the securing element 450 may be placed above the printed circuit board 440.

The printed circuit board 440 may thus be arranged between the base 430 and the securing element 450. The securing element 450 may include inclined surfaces 453 which interact with counter surfaces 432a, 432b of the base 430. In this embodiment, the securing element 450 may be pressed downwards onto the printed circuit board 440 by the preloading discussed herein, so that the taper 452 of the securing element 450 may be pressed onto the heating element 41 from above. The securing element 450 may be mounted on the base 430 via a groove in the securing element 450 and a cam 431 of the base 430, as described in the embodiment according to FIGS. 1-10.

REFERENCE LIST 1 patch pump/infusion administration device
2 disposable unit
3 reusable unit
4 reservoir
5 power supply unit
10, 110, 210, 310, 410 piercing device
15 projections
20 guide cylinder
21 hard cannula
22 hard cannula holder
23 soft cannula
24 soft cannula holder
25a, 25b arms
26a, 26b tabs
27 opening
28 stop
29 contact surface
30, 130, 230, 330, 430 base
31, 431 cams
32a, 32b, 432a, 432b mating surfaces 33 guide
34 mandrel
40, 140, 240, 340, 440 circuit board
41 heating element
50, 150, 250, 350, 450 securing element
51 opening
52, 152, 252, 452 taper
53, 453 inclined surfaces
60, 160, 260, 360 retaining element
61 nose
62 securing surface
63 pin
70 return spring
80 piercing spring/elastic element
90 position detector
135, 235 bearing pin
154, 254 pin
155a, 155b, web
255a, 255b, 255c web
164, 264, 364 opening
356 groove
357 web

What is claimed is:

1. A piercing device for an administration device, the piercing device comprising:
   a biased elastic element applying a biasing force for generating a piercing movement;
   a base;
   a cannula unit movable relative to the base from a secured position in a piercing direction, wherein the cannula unit is biased in the piercing direction by the biasing force of the biased elastic element;
   a securing element configured to hold the biased cannula unit in the secured position, wherein the securing element comprises a thermosensitive area configured to be deformable when heated under mechanical tension;
   a retaining element configured as a rotatable lever, wherein in the secured position the retaining element is adapted to transfer the biasing force to the securing element; and
   a heating element,
   wherein the securing element is arranged in a stack between a surface of the base and an underside of the heating element, and wherein the heating element is configured to heat the thermosensitive area of the securing element such that the thermosensitive area can deform due to the biasing force,
   wherein upon deformation of the securing element, the biasing force of the elastic element causes a movement of the cannula unit away from the secured position in the piercing direction, and
   wherein during the movement of the cannula unit, the cannula unit causes the retaining element to rotate such that the piercing movement is triggered.

2. The piercing device according to claim 1, wherein the securing element comprises an inclined surface which, in the secured position of the cannula unit and due to the biasing force, interacts with a counter-surface such that the thermosensitive area of the securing element is pressed against the heating element.

3. The piercing device according to claim 1, wherein the securing element is configured as a unitary component, the securing element comprising a first end coupled to the base, a second end coupled to the retaining element, and the thermosensitive area arranged between the first end and the second end.

4. The piercing device according to claim 1, wherein the heating element is integrated in a printed circuit board.

5. The piercing device according to claim 1, wherein the securing element comprises an elongated shape with a taper in the thermosensitive area, and wherein the securing element is arranged such that the taper and the heating element at least partially overlap.

6. The piercing device according to claim 1, wherein the cannula unit comprises a first cannula and a second cannula, wherein the second cannula receives a second biasing force from a second biased elastic element, wherein the second biasing force is applied counter to the piercing direction.

7. The piercing device according to claim 6, wherein the first elastic element and the second elastic element are arranged coaxially relative to one another.

8. The piercing device according to claim 7, wherein one of the first elastic element or the second elastic element is arranged at least partially within the other of the first or second elastic elements.

9. The piercing device according to claim 6, wherein the first elastic element and the second elastic element are each configured as a spring.

10. The piercing device according to claim 6, wherein the cannula unit with the first cannula, the second cannula and the second elastic element is configured to be moved from the secured position into a piercing position, and the second cannula is configured to be moved away from the piercing position by the second biasing force while the first cannula remains in the piercing position.

11. The piercing device according to claim 1, further comprising a position detector configured to determine whether the cannula unit has moved out of the secured position, wherein the position detector is configured to be actuated by a movement of a cannula holder of the cannula unit.

12. An administration device comprising a disposable unit and a reusable unit, the disposable unit comprising a reservoir and the piercing device according to claim 1, wherein the piercing device is fluidically connected to the reservoir.

13. A piercing device for an administration device, the piercing device comprising:
   a first biased elastic element applying a first biasing force for generating a piercing movement in a piercing direction;
   a second biased elastic element applying a second biasing force for generating a movement counter to the piercing direction;
   a base;
   a cannula unit comprising a first cannula and a second cannula, wherein the cannula unit is movable relative to the base from a secured position in the piercing direction, wherein the cannula unit is biased in the piercing direction by the first biased elastic element, and wherein the second cannula is biased counter to the piercing direction by the second biased elastic element;
   a securing element configured as a unitary component, the securing element comprising a first end coupled to the base, a second end, and a thermosensitive area arranged between the first end and the second end and configured to be deformable when heated under mechanical tension, wherein the securing element is configured to hold the biased cannula unit in the secured position, and wherein the securing element is biased by the first biased elastic element;
   a retaining element coupled to the second end of the securing element and configured as a rotatable lever, wherein in the secured position the retaining element is adapted to transfer the first biasing force to the securing element; and a heating element configured to heat the thermosensitive area of the securing element such that the thermosensitive area can deform due to the first biasing force exerted on the securing element by the first biased elastic element, wherein upon deformation of the thermosensitive area, the first biasing force causes a movement of the cannula unit away from the secured position in the piercing direction, wherein the movement of the cannula unit forces the retaining element to rotate such that the cannula unit is moved further under the first biasing force to a piercing position, and upon the cannula unit reaching the piercing position, the second cannula is configured to be moved away from the piercing position under the second biasing force to a retracted position while the first cannula remains in the piercing position.

14. The piercing device according to claim 13, wherein the first biased elastic element and the second biased elastic element are each configured as a spring, wherein the springs are arranged coaxially relative to one another, and one of the springs is arranged at least partially within the other of the springs.

15. The piercing device according to claim 13, wherein the securing element is arranged such that the thermosensitive area and the heating element at least partially overlap, and wherein the thermosensitive area and the heating element contact one another.

* * * * *